united States Patent [19]
Poley

[11] Patent Number: 4,819,631
[45] Date of Patent: Apr. 11, 1989

[54] FOLDED INTRAOCULAR LENS, METHOD OF IMPLANTING IT, RETAINER, AND APPARATUS FOR FOLDING LENS

[76] Inventor: Brooks J. Poley, 2 Greenway Gables, Minneapolis, Minn. 55403

[21] Appl. No.: 184,432

[22] Filed: Apr. 21, 1988

Related U.S. Application Data

[62] Division of Ser. No. 31,250, Mar. 26, 1987, Pat. No. 4,769,034.

[51] Int. Cl.4 .............................................. A61B 17/00
[52] U.S. Cl. ..................................... 128/303 R; 623/6
[58] Field of Search ........................ 623/6; 128/303 R

[56] References Cited

U.S. PATENT DOCUMENTS

| 4,451,938 | 6/1984 | Kelman . | |
|---|---|---|---|
| 4,573,998 | 3/1986 | Mazzocco . | |
| 4,605,409 | 8/1986 | Kelman . | |
| 4,636,210 | 1/1987 | Hoffer . | |
| 4,681,102 | 7/1987 | Bartell | 128/303 R |
| 4,702,244 | 10/1987 | Mazzocco | 128/303 R |
| 4,747,404 | 5/1988 | Jampel | 128/303 R |

OTHER PUBLICATIONS

"Soft IOL Technology: The New Frontier" by V. L. Bohn, Ocular Surgery News, vol. 5, No. 5, 3/1/87.
"Pathologic Findings of an Explanted Silicone Intraocular Lens" by Donald A. Newman, M.D., et al, *J. Cataract Refract. Surg.*, vol. 12, May 1986, p. 292.
"Implantation Procedure for the Bechert 7 mm One-Piece Posterior Chamber Lens" by Chas. H. Bechert, M.D., Precision-Cosmet Co., Inc.
"The Second Generation Small Incision Silicone IOL" from Allergan Medical Optics.

*Primary Examiner*—Richard J. Apley
*Assistant Examiner*—James Prizant
*Attorney, Agent, or Firm*—Wood, Herron & Evans

[57] ABSTRACT

An intraocular lens is folded on itself one or more times and is releasably held in the folded configuration by a very small, flexible retainer so as to be implantable in an eye through a smaller incision than would otherwise be required. The retainer is secured around the folded lens in a transverse direction and is held taut by the resiliency of the lens. The retainer is released in the eye as by severing, following which the lens is unfolded and positioned in the eye and the retainer is removed. The technique is especially useful following removal of a cataract by the phako-emulsification technique, because the same small incisions can be used for implanting the lens.

7 Claims, 5 Drawing Sheets

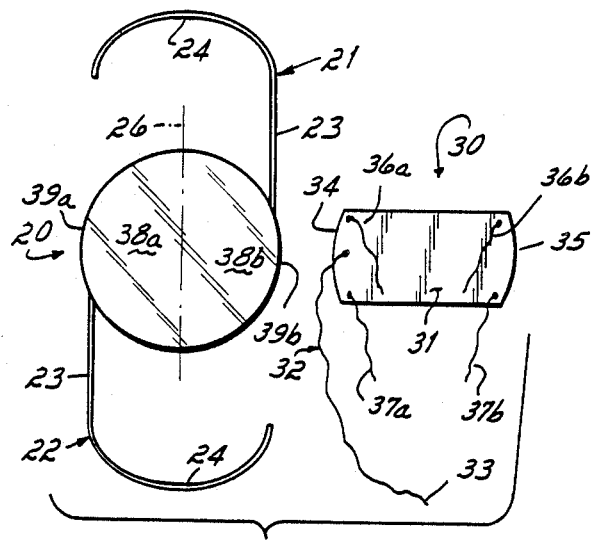
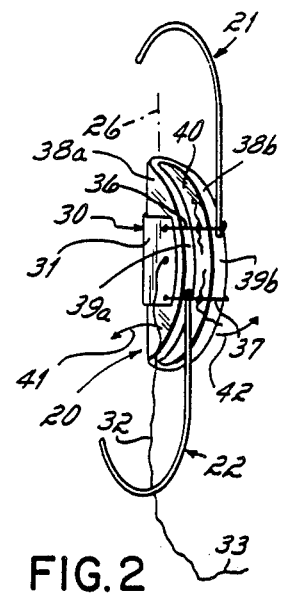
FIG. 1   FIG. 2
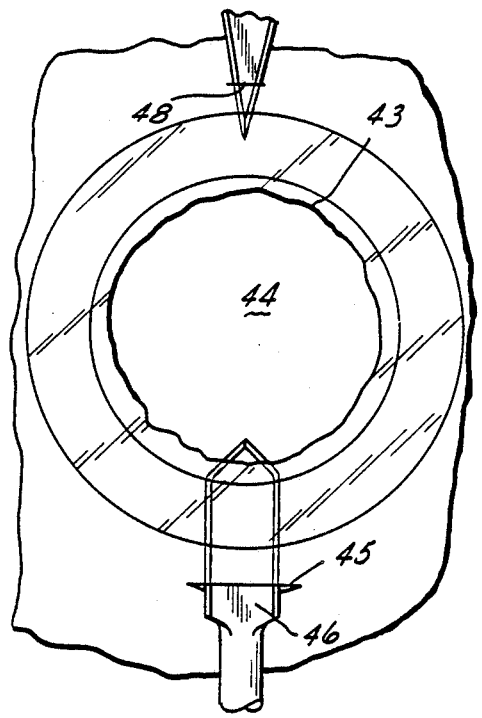
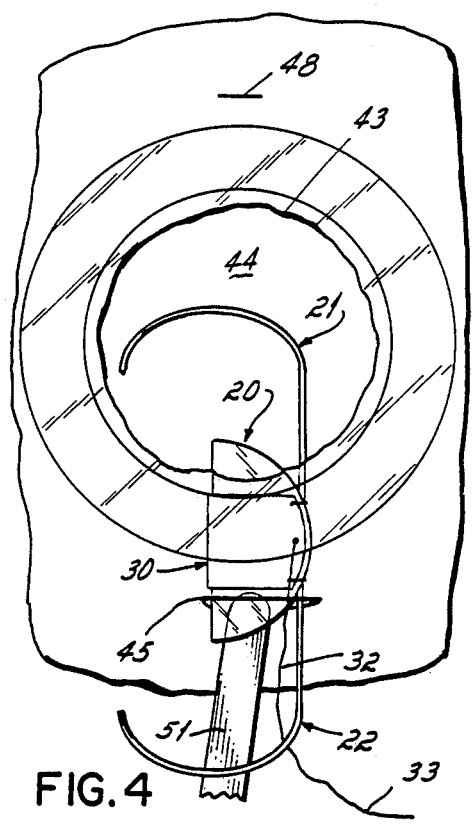
FIG. 3   FIG. 4

FOLDED INTRAOCULAR LENS, METHOD OF IMPLANTING IT, RETAINER, AND APPARATUS FOR FOLDING LENS

This is a division of application Ser. No. 31,250, filed Mar. 26, 1987, now U.S. Pat. No. 4,769,034.

FIELD OF THE INVENTION

This invention relates generally to the implantation of intraocular lenses. More specifically it relates to a method of implanting a lens which is folded for implanting; a retainer for holding the lens in the folded configuration; and a device for folding the lens and holding it while the retainer is secured about it.

BACKGROUND OF THE INVENTION

The use of intraocular implant lenses has been highly developed in recent years, especially in connection with the removal of cataracts, and such operations are now common medical procedure. In such procedures it is desirable to minimize the size of the incisions which must be made to insert and position the lens in the eye, in order to reduce healing time and minimize any chance of wound failure.

Most previous implanting techniques have required that the incision which is made in the eye have a width equal to or greater than the diameter of the implant lens, so that the lens can be inserted through the incision. Recently techniques have been developed for "folding" or otherwise reducing the width of certain lenses prior to incision, then inserting the folded lens through the incision and unfolding it within the eye, see Bohn, "Soft IOL Technology", *Ocular Surgery News*, Mar. 1, 1987, page 1, and U.S. Pat. No. 4,636,210 to Haffer, issued Jan. 13, 1987. However, so far as I am aware there has not previously been known a technique whereby a lens could be folded and held in the folded condition by a retainer which does not add significantly to its size, inserted into the eye in the folded configuration with the retainer around it, and the retainer thereafter released as by severing it within the eye so that the lens could be unfolded within the eye, and wherein the resiliency of the lens itself effects unfolding with only minimal manipulation required for control of the lens as it unfolds.

BRIEF DESCRIPTION OF THE INVENTION

This invention does not require a new type of lens; that is, it can be practiced with resilient foldable intraocular lenses of types already known per se. In accordance with the invention, the lens is first folded about an axis of folding. The lens is folded but not creased; after folding it remains resiliently unfoldable. Preferably the lens is folded once, like a "taco." Two folds can be used, but such a folding procedure is more difficult in practice, and it is also more difficult to unfold and position a multiply-folded lens. It is important to note that by "folding," it is not meant that the lens be rolled up spirally like a window shade. Unlike a spiral, the lens surfaces on either side of the axis of folding are substantially parallel after folding, that is, they are not curved apart from the lens curvature itself. This has important advantages in unfolding, as will be seen.

The diameter of conventional foldable lenses is typically about 7 millimeters, whereas the dimension of the folded lens, measured transverse to the axis of folding, is substantially less, e.g. about 3.2 mm. for a single fold, and less if folded twice.

The folded lens is inherently resilient and tends to unfold itself if not held in the folded condition for implantation. As a means of retaining the folded lens, I have provided a releasable retainer which encircles the lens like a releasable band or yoke. The retainer may be formed of thin flexible material which, at least in part, can be a fine suture-like material or thin flexible material, and is held taut by the outward or unfolding force of the lens. The retainer does not substantially add to the effective size of the folded lens, but holds the lens so that it can be inserted into the eye through a smaller incision than would otherwise be required.

After the lens has been inserted, the retainer is released within the eye itself so that the lens is freed from the retainer. The lens is then unfolded within the eye, and is centered or positioned by conventional spring-like haptics or another centering device which can be of known type. The retainer is then withdrawn, leaving the lens unfolded and seated within the eye.

It is a particular advantage of this invention that it is especially useful following the phako-emulsification technique for removing a cataract, although it is not limited to such use. As practiced at the present time, the phako-emulsification technique requires making a surgical incision for the standard emulsification tool by which the cataract is broken up and removed. This incision can be as small as approximately 3.2 millimeters in width. An unfolded lens is wider than this, so that a larger incision is required for an unfolded lens than is required for cataract removal. Pursuant to this invention, an opening no larger than is required for the cataract removal can be used for insertion of a lens which is held in folded condition by a retainer around it. This is a substantial advantage in terms of minimizing any possible adverse effects of the incision into the eye.

As indicated above, foldable intraocular lenses are of flexible resilient material, typically silicone. As a result of its resiliency the folded lens tends to unfold itself spontaneously, even within the eye itself. Lens unfolding must be controlled lest the lens spring open in an abrupt manner and in the act of doing so, possibly damage the cornea or other part of the eye. I have provided a retainer which can be released, and subsequent lens unfolding can be effectively controlled, by the use of a second instrument which is inserted into the eye through a small secondary incision. The secondary incision can be the same secondary incision which is regularly used in the phako-emulsification. The second instrument can also provide a double function: it can be used first to release a releasing portion of the retainer (as by cutting), then to control unfolding of the lens.

Related aspects of the invention comprise the retainer itself, and the lens held folded by such a retainer. In preferred embodiment the retainer comprises a pliant band having a width about ½-¾ the diameter of the lens and having a length slightly less than the diameter of the lens. This band encircles the folded lens transversely to the axis of folding. The retainer has one or more ties or other releasing means for securing the ends of the band together, thereby to hold the lens folded. An elongated filamentary tail extends from the band for removal of the retainer from the eye after the lens has been freed from the retainer. The tail is preferably of sufficient length that it will extend out the primary incision so that it can be grasped from outside the eye for removing the retainer from the eye.

The edges of the lens opposite the axis of folding are spaced apart; that is, there is a "gap" or space between them. Ties or another releasing portion of the retainer preferably extend taut across this gap and thus are accessible for cutting or releasing without damage to the lens surface by the releasing instrument.

The releasing portion of the retainer may simply comprise a suture-like material (e.g., a short length of #10 gauge suture) which, when secured, can be cut to release the lens. A hook-shaped cutting knife is preferred as the releasing instrument; or a miniature scissors can be inserted through the secondary incision to cut the releasing portion. When the releasing portion is cut, the lens starts to unfold and the releasing implement is then used to control the unfolding of the lens.

In still another aspect of the invention I have provided a "press" or lens folding device by which the tiny lens can be folded and held while the retainer is secured around it. I have found that, because of the small and delicate nature of these lenses it is extremely difficult to do the folding merely with the fingers; it is difficult both to fold the lens and to hold it in the folded condition without injuring it while tying or securing the retainer around it. In preferred form this lens folding device comprises a base having a seat or shelf on which both the retainer and the lens are positioned for folding. A swing arm is mounted to swing approximately 180° from below the lens upwardly and across its top, thereby to fold the lens and retainer about the desired axis of folding. An abutment or stop holds the lens from sliding away as it is engaged by the swing arm. The arm has a pocket with a lip that receives and captures the lens at a position opposite the abutment, causing the lens to fold between the lip and the abutment. The lens can be folded with the retainer around it; the releasing means are accessible through the swing arm and base, and can be secured while the lens is held folded in the press.

DESCRIPTION OF THE DRAWINGS

The invention can best be further described by reference to the accompanying drawings, in which:

FIG. 1 is a front view, greatly enlarged in size, of one type of lens adapted for use in the practice of the invention, and a preferred form of retainer;

FIG. 2 is a perspective view of a lens and retainer of the types shown in FIG. 1, held in singly folded configuration by the retainer tied around it;

FIGS. 3-8 are a series of diagrammatic views, enlarged in size, showing the sequence of making the incisions, inserting, unfolding and seating the lens, and removing the retainer in accordance with a preferred method of practicing the invention;

More specifically, FIG. 3 is an enlarged fragmentary view of an eye, showing the manner in which primary and secondary surgical incisions are made for a preferred method of practicing the invention;

FIG. 4 is a view similar to FIG. 3 but shows the lens, held in the retainer, being inserted into the eye;

FIG. 5 shows the releasing means being severed by one type of releasing instrument;

FIG. 6 shows the retainer after it has been freed by a different type and position of releasing instrument, the unfolding of the lens being controlled by this alternative releasing instrument;

FIG. 7 shows the lens as unfolded in the eye and the retainer being removed through the primary incision;

FIG. 8 shows the lens centered in position in the eye by the haptics;

More specifically, FIG. 10 shows the manner in which the releasing instrument of FIG. 5 is used to cut the retaining means of a doubly folded lens;

FIG. 11 showing the lens of FIG. 10 being unfolded under the control of the releasing instrument;

FIG. 12 shows the further unfolding of the lens about the second axis of folding;

DETAILED DESCRIPTION

Figure 5:
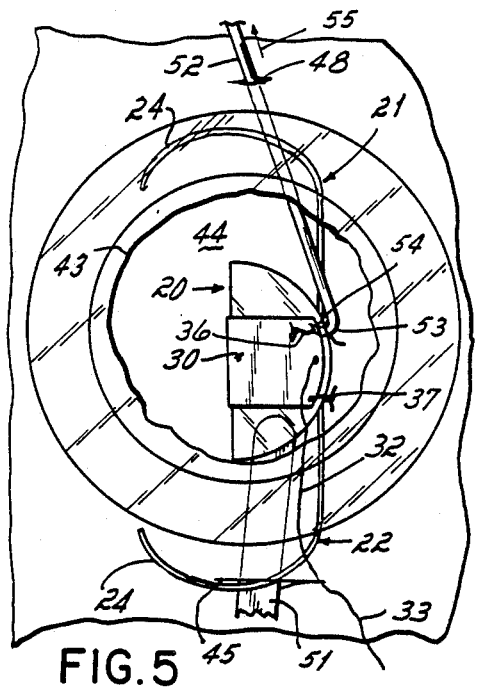

As noted above, the invention can be practiced with various types of already existing foldable lenses. FIGS. 1-12 and 17-18 illustrate the use of a preferred form of lens; while FIGS. 13-16 show the use of two other types of foldable lenses.

The preferred type of lens for use in the invention is indicated generally by 20, and is circular in outline, and has a conventional lens sectional shape (see FIG. 17), and two haptics 21, 22, which extend from it at diametrically opposite points. The particular lens shown is of the general type sold by Allergan Medical Optics Division of Allergan, Inc., of Irvine, Calif., under their designation "Second Generation Small Incision Silicone IOL." The lens has two haptics 21, 22, which are hook-shaped, each having a shank portion 23. The shanks of the two haptics are parallel to one another but spaced apart laterally. Each haptic has a hook-shaped end portion 24. It will be noted that in the unfolded configuration the end portion 24 of upper haptic 21 curves to the left, whereas the lower haptic 22 extends toward the right, that is they face in opposite directions. When the lens is folded, as will be described, both haptics face in the same direction (compare FIGS. 2 and 4).

These lenses are made of a resilient flexible material, for example silicone, and can be folded about an axis of folding which, in the preferred form, is a central axis midway between the shanks 23, 23 of the two haptics, as indicated by imaginary line 26.

A preferred form of retainer is designated by 30 in FIG. 1. This retainer includes a lens encircling portion 31 in the form of a band or strip of flexible thin sheet material, for example of "Tyvek" brand high density polyethylene. The width of this band, that is, its transverse dimension, is preferably ¼ to ¾ of diameter of lens 20. A flexible spine portion 32 is secured at one end to band 31 of retainer 30. This tail can be made of suture-like material, and should be long enough that at least its outer end or tail 33 will extend outside the eye so that it can be grasped to withdraw the retainer from the eye after the lens has been released.

Retainer 30 preferably includes two opposed pairs of ties or releasing portions for joining its ends 34 and 35. Ties 36a and 36b are secured together (FIG. 2) to form one releasing portions, and ties 37a and b form a second releasing portion. These releasing portions can be of a suture-like material, as can spine 32, and when secured around the lens hold it in folded configuration.

A lens of the type shown in FIG. 1 is shown in its preferred single fold configuration in FIG. 2, and is held in such position by a retainer of the type shown in FIG. 1. The lens is folded about a single, central axis of folding 26. As can be seen, the lens is not spirally wound; on each side of axis of folding 26 the lens portions or halves 38a and b are essentially parallel (neglecting their optical curvature), unlike a spirally wound lens. The opposite sides 38a, 38b of the lens, are adjacent and overlie one another, as shown in FIG. 2, and are separated by a gap 40. It will be noted that the lens is not creased along the axis of folding; the material is sufficiently resilient that its halves tend to unfold in the direction of arrows 41, 42, when not restrained. The lens is held against such unfolding by retainer 30, which extends across the lens, transversely to axis of folding 26. The outer ends 34 and 35 of retainer band 31 generally correspond in outline to that of the lens edges 39a and b but do not extend beyond the lens. Tie 36a is tied to opposite tie 36b; similarly tie 37a is tied to its opposite member 37b, as by conventional surgeon's knots. The ties extend across gap 40 and are generally held taut by the tendency of the lens halves to unfold.

It can be seen that the releasing portions are readily accessible in gap 40 between the lens halves, so that they can be released as by shearing with a knife or scissors.

The series of steps involved in implanting a lens in accordance with this invention, particularly in the preferred configuration shown in FIG. 2, is illustrated in sequence in FIGS. 3-8. As mentioned previously, this type of implanting technique is especially useful following removal of a cataract in the eye by the phako-emulsion technique, although it is not limited to such use. For purposes of the following discussion, it is therefore assumed that a phako-emulsification is performed, although it should be understood that this implantation technique is useful whether or not a cataract has been removed, and regardless of the particular technique by which the cataract is removed.

The top cover of the lens pocket is 44 first cut away in accordance with conventional procedure, leaving an irregular lens pocket edge designated at 43. A primary incision 45 is formed by a blade-shaped primary cutting instrument 46. Phako-emulsification requires an opening which is 3.2 millimeters or slightly larger, and accordingly, incision 45 may be formed to just the width required for the phako-emulsification tool to be inserted. The opening need not be enlarged then or thereafter to accept the full diameter of an unfolded lens.

The practice of this invention usually requires that a secondary surgical incision also be made, for insertion of an implement to release the releasing means and to control the unfolding and positioning of the lens. In the method shown in FIGS. 3-5, 7 and 8, a secondary incision 48 is formed diametrically opposite primary incision 45; but it is substantially narrower, suitably about 1.5 mm. In the presently preferred method shown in FIG. 6, the secondary incision is formed about 90° to the right of the primary incision. Those skilled in the art of cataract removal will recognize that phako-emulsification also requires a secondary incision for manipulation of the cataract during its removal. The secondary incision required for cataract removal can comprise the same secondary incision 48 for releasing the retainer.

FIG. 4 illustrates the insertion of the unfolded lens into the lens pocket 44 through primary incision 45. The lens is held by a primary instrument comprising a forceps 51, which grips the lower lens half only. The hooked end 24 of lower haptic 22 remains outside the incision until the lens has been unfolded. As a single fold lens unfolds, the orientation of the lower haptic reverses by 180°; hook end 24 faces to the left in FIG. 4, before the lens has been unfolded, but after the lens has been unfolded as in FIG. 7 the same haptic hook faces to the right. The lower haptic hook end 24 must project outside incision 45, so that it can rotate freely as the lens is unfolded.

Figure 6:
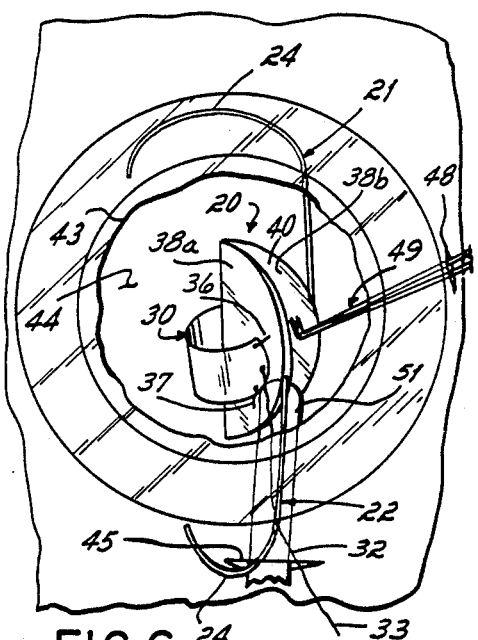
Figure 7:
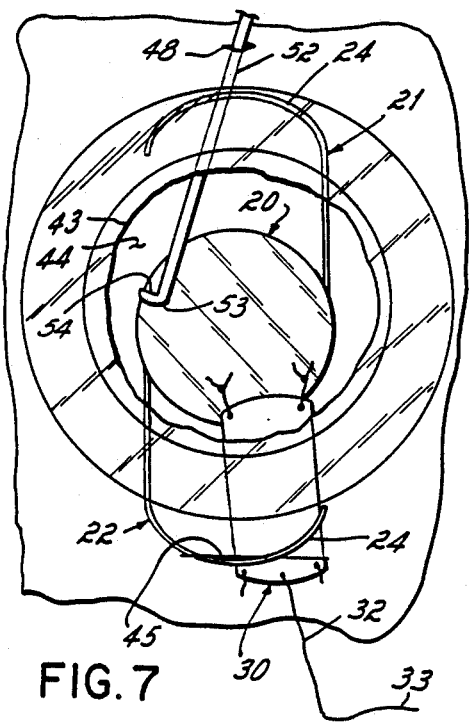
Figure 8:
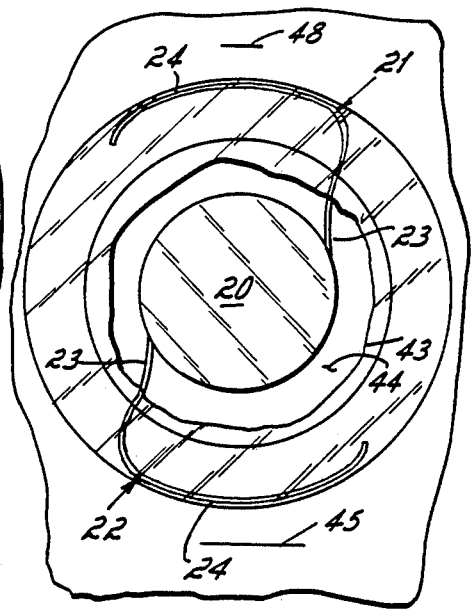

As the lens is inserted the upper haptic 21 is seated in lens pocket 44, essentially opposite primary opening 45 (FIG. 5). The releasing means 36, 37 are released with a releasing means in the form of a second instrument 52. This second instrument 52 can be of alternate forms; it is presently preferred that it be a scissors 49, as shown in FIG. 6; but alternatively a knife can be used, having a hook-shaped distal end 53 with a sharp cutting edge 54 on the inside of the hooked end 53. The cutting edge is effectively shielded by the outer side of hooked end 53, so that it is not engaged until it is drawn in the direction of the arrow 55 in FIG. 5. With the lens in place, cutting edge 54 is hooked over the tied releasing means 36a,b and is pulled in the direction of arrow 55 to sever it. As this occurs it can be seen that the lens is held in tension against movement, being pulled in one direction by forceps 51 and in the opposite direction by cutter 52. After one releasing means 36a, 36b is cut, the other releasing means 37a,b is then cut. In either type of releasing operation the lens surface is not damaged by the cutting, because the releasing means are stretched taut between the lens halves and do not lie against the lens.

Release of the releasing portions frees the lens, and the lens spontaneously begins to unfold within the eye, as illustrated in FIG. 6. In order to guide and control the movement of lens half 38a as it unfolds, the end of second implement 49 or 52 is engaged with the lens. As the lens unfolds, the retainer, which is no longer tied to the lens, is simply pushed aside within the lens pocket.

As the lens continues to unfold, it will be noted that the end of haptic 22, which faced toward the left in FIG. 5, turns with its lens half 38a and ultimately faces toward the right (FIG. 7), its end 24 having been free to rotate outside the eye. At this point the retainer can be removed (FIG. 7) by gripping its tail 33. The unfolded lens is then centered within the eye and haptic 24 is seated within the lens pocket (see FIG. 8), in accordance with known practice.

In the method just described the lens is folded about a single axis of folding and is held by a retainer having a band-shaped encircling portion 31. FIGS. 9-12 illustrate a second method of practicing the invention wherein the lens was folded twice, about separate parallel axes of folding and is held so folded by a modified form of retainer.

In this method the lens, which may be of the same type as that designated by 20 in FIG. 1, is folded about two parallel axes 60 and 61, which effectively define three portions of the folded lens. As viewed in FIG. 9, the left third 62a of the lens is first folded over the central lens portion 62b, following which the right lens portion 62c is folded over left portion 62a. Both a double folding and a double unfolding are required. It should also be noted that, unlike the singly folded lens shown in FIG. 2, in the folded configuration of FIG. 9, the haptic ends 24, 24, face in opposite directions.

Figure 9:
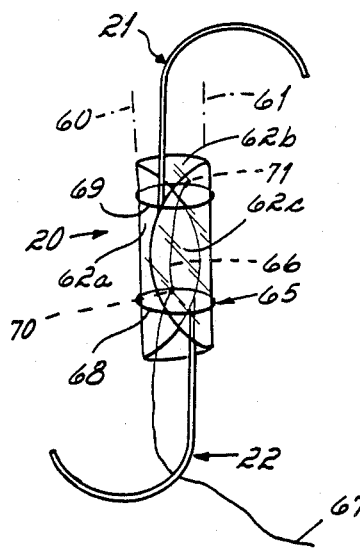
FIG. 9 illustrates an alternative method of practicing the invention, wherein the lens is folded about two parallel axes of folding and is held by a different type of retainer.
Figure 10:
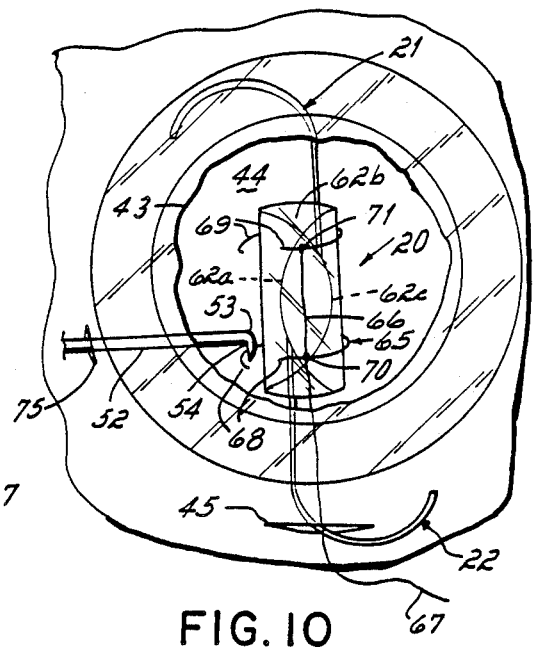
FIGS. 10, 11 and 12 are a sequence of views similar to FIGS. 3-8, but show implanting a doubly folded lens of the type shown in FIG. 9.
Figure 11:
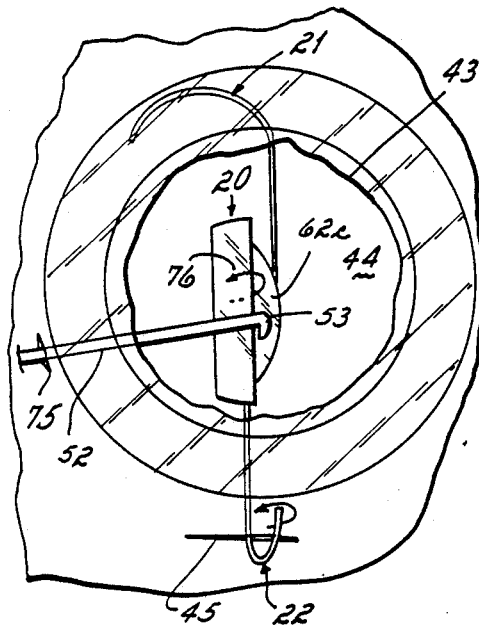

FIG. 9 shows an alternative form of retainer 65 which differs from that shown in FIG. 1 in that it does not have an encircling band but rather is formed entirely of suture material. This alternative retainer, includes a central spine portion 66 having a tail portion 67. Two transverse releasing portions 68 and 69 are joined to the spine portion 66 at spaced positions and extend transversely to the folded lens. Each releasing means 68, 69, comprises a short length of suture material which extends around the folded lens and is tied to itself by knots 70 and 71. This modified configuration is less convenient in that two folds must be made and, moreover, the knots 70, 71 lie closer to the lens surface; there is not so large a gap between the overlying lens portions 62c and 62a. Thus it is harder to tie and to release this configuration. The advantage is, of course, that the width of the folded lens is even less than that of the single fold (FIG. 2) configuration.

Figure 12:
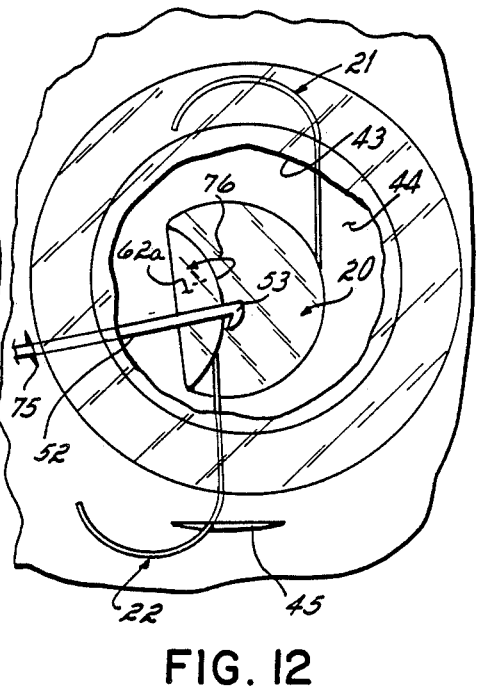

In implanting a doubly folded lens, a primary incision 45 is formed as before (although it can be made correspondingly narrower if additional width is not otherwise required). It should be noted that because of the double unfolding which is required, lens portion 62c, from which haptic 21 projects, is placed downwardly (as viewed in FIG. 10) within the lens pocket. A secondary incision 75 is made which need not be diametrically opposed to primary incision 45, but can be spaced angularly from it, at an angular separation of 30° to 180°. A cutting instrument 52 is inserted through incision 75, and the releasing portions 68, 69 are severed. (If scissors 49 is used to remove the retaining sutures, the secondary incision should be made on the right side, about 90° from the primary incision. Inserting the scissors from the right side allows the blades to cleanly engage the retaining suture in gap 40 between the two lens halves 38a and 38b.) The lens is unfolded to the left, as indicated by arrow 76. Lens center portion 62b is first unfolded 180° about axis 61; then portion 62a is rotated another 180° to unfold it about axis 62 (FIG. 12). Second instrument 48 or 52 may be used to guide the unfolding as before. During unfolding the end of haptic 22 rotates outside incision 45 for rotation. The retainer 65 is removed and the lens is seated, as already explained.

Figure 13:
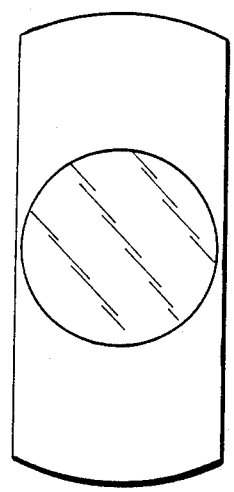
FIG. 13 is an enlarged plan view of a second type of foldable lens, suitable for use in the invention.
Figure 14:
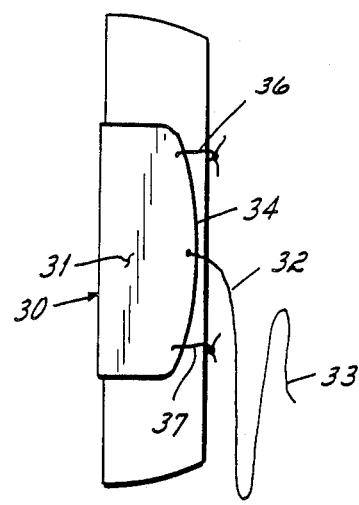
FIG. 14 is an enlarged plan view of a singly folded lens of the type shown in FIG. 13, held folded by a retainer of the type shown in FIG. 1.
Figure 15:
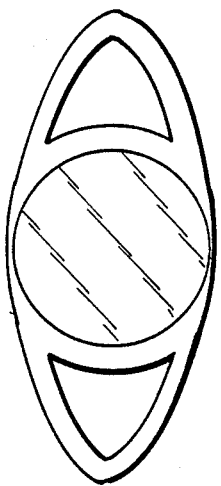
FIG. 15 is an enlarged plan view of a third type of foldable lens suitable for use in the invention.

FIGS. 13-15 show two other known types of foldable intraocular lens in both unfolded and folded configurations. These lenses, in contrast to the lens of FIG. 1, do not include filamentary haptics. The lens shown in FIGS. 13 and 14 is of the type sold by Coopervision - Cilco, Inc., under its designation Nova-Soft II, 960 series. It is shown in FIG. 14 held folded by a retainer 30 which is secured around the lens transversely to a central axis of folding. The releasing portions 36, 37 extend across a space between the overlying longitudinal edges of the lens.

Figure 16:
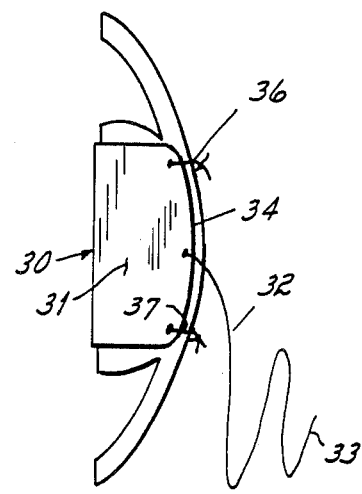
FIG. 16 is an enlarged plan view of a folded lens of the type shown in FIG. 15, held folded by a retainer of the type shown in FIG. 1.

The lens shown in FIGS. 15 and 16 is of the type made by Staar Surgical, sold under its designation Model 4004. Both these lenses are more suited to be folded once, than twice.

Figure 17:
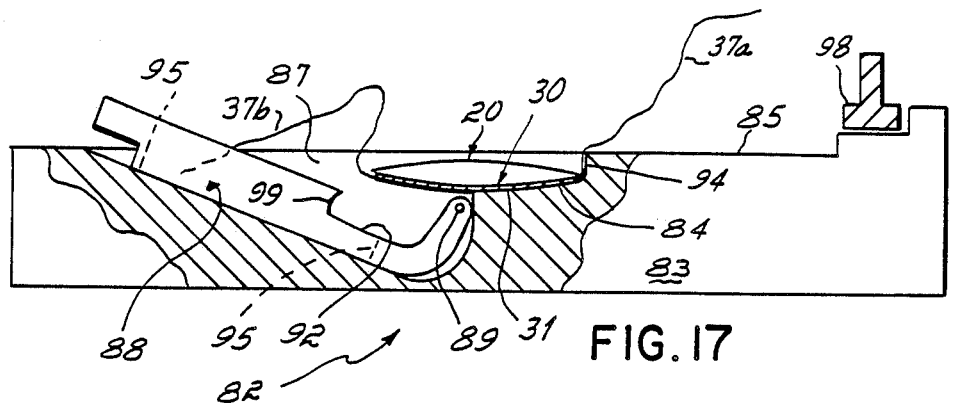
FIG. 17 is a side view, partly in section, of a preferred form of application for folding the lens.
Figure 18:
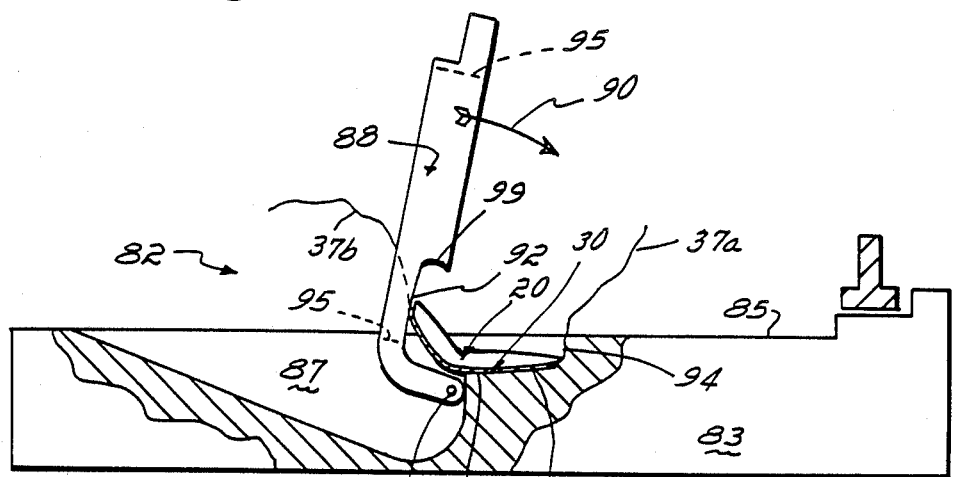
FIG. 18 is similar to FIG. 17 but shows the arm of the folding apparatus being swung about its hinge, to fold the lens about a single central axis of folding.

Because of the small size of the lens and the awkwardness of holding the lens in the folded condition while securing the retainer around it, I have provided a special lens folding "press" for this purpose. This apparatus, designated by 82 in FIGS. 17-19, has a base 83 which presents an upwardly facing lens shelf or seat 84 which is spaced below top surface 85 by approximately the thickness of the lens. Seat 84 is particularly shaped to support and hold positioned a lens of a specific configuration, e.g., semicircular to support a lens 20. It will be noted that seat 84 supports only about half the width of the lens, i.e., a first portion which is the right lens half as seen in FIG. 17. The left lens half, or second portion, projects outboard over a cavity 87. A retainer 30 is placed on the seat under the lens with its encircling means 31 and releasing means 37a and b extending lengthwise, i.e., left to right in FIG. 17.

Figure 19:
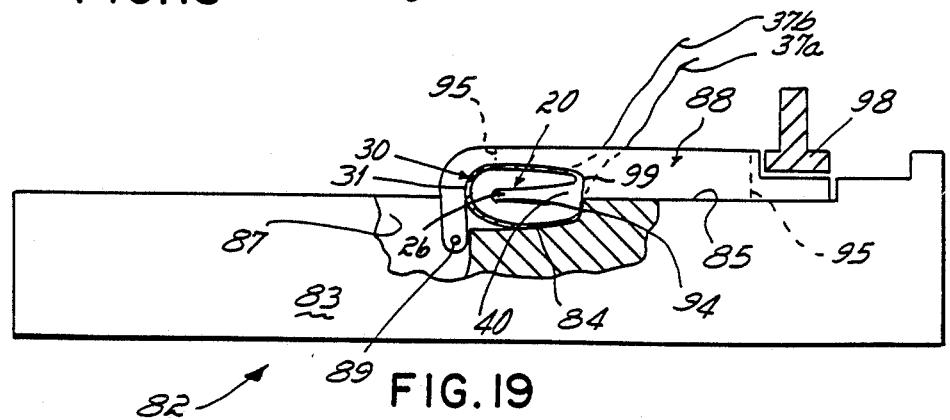
FIG. 19 is similar to FIGS. 17 and 18 but shows the lens held folded by the arm so that the releasing means of the retainer can be secured to hold the lens in its folded configuration.

Press 82 has a swing-arm or folding handle 88 which is hinged for rotation about a transverse pivot axis 89 in cavity 87, offset below the folding axis. When swing-arm 88 is swung up and out of the cavity, i.e., clockwise as designated by arrow 90 in FIG. 18, a lens receiving and engaging pocket 92 on handle 88 engages the outboard portion of the lens and the retainer under it, and folds them about an axis of folding at 26 (see FIG. 19). As the lens is folded it bears against an abutment 94 or semicircular wall around seat 84 which holds it against rightward displacement. As can be seen in FIG. 19, lens engaging pocket 92 has a lip 99 which captures the lens edge. Arm 88 is shaped so that when it is rotated to the lens folded position, the pocket folds the outboard half of the lens toward the abutment and then holds it in the folded configuration shown in section in FIG. 19.

Arm 92 has an open center, the edges of which are indicated by the dashes at 95. When the lens has been folded the releasing portions 36 and 37 are accessible through the open center of arm 88 and can be tied together to hold the lens folded. A slide bar or clamp, indicated generally by 98, is engageable with an end of the arm to hold it down in the lens folding position as shown in FIG. 19.

Thus it will be seen that the lens folding press folds the lens, properly positions the retaining means about the folded lens, and holds the lens and retainer in folded attitude while the releasing portions are tied across the space 40 between the lens edges. The press can be injection molded and assembled at low cost to provide a disposable device which can be supplied with each lens if desired. The unfolded lens may be supplied to the physician already seated in this device, on the retainer and ready for folding, so that it can be folded and the retainer secured immediately prior to implanting. (This may be desirable to minimize any chance of deformation of the lens resulting from storage in the folded configuration.) Alternatively, of course, the lens may be folded at the point of manufacture.

The various aspects of invention have been described in their preferred embodiments, but those skilled in the art will understand that the invention is not limited to those forms, and extends to other embodiments within the scope of the claims which follow.

What is claimed is:

1. Apparatus for folding an intraocular lens about a transverse axis of folding, comprising, a base presenting a lens seat shaped to support a first portion of said lens on one side of said axis of folding, a second portion of the lens extending off said seat and over a cavity in said base, an abutment adjacent said seat to hold the lens from moving off the seat during folding, a swing arm mounted for rotation about a pivot axis which is parallel to but offset from said axis of folding, said arm being swingable about said pivot axis to a lens folded position, said swing arm having a pocket which receives and engages said second portion of said lens as said arm is swung about said pivot axis, said pocket urging said second portion toward said abutment as the arm is swung about the pivot axis.

2. The lens-folding apparatus of claim 1 wherein said base presents a cavity over which said second portion of the lens extends, said pivot axis being offset below said axis of folding and extending across said cavity, said arm being swingable between a first position in said cavity on one side of said pivot axis and below said second lens portion, and a lens folding position above said seat and on an opposite side of said pivot axis.

3. The lens-folding apparatus of claim 1 wherein said pocket has a lip which holds said second portion of the lens as said arm is swung about said pivot axis.

4. The lens-folding apparatus of claim 1 wherein said abutment is an upstanding wall around said seat.

5. The lens-folding apparatus of claim 1 wherein said swing arm is L-shaped in longitudinal section and has parallel legs, said legs straddling said second lens portion.

6. The lens-folding apparatus of claim 1 wherein said arm has an open center portion through which the folded lens is accessible to be secured in a retainer.

7. The lens-folding apparatus of claim 1 further comprising a clamp for holding the swing arm in said lens folded position.

* * * * *